United States Patent [19]

Whitehouse et al.

[11] Patent Number: 5,509,802
[45] Date of Patent: Apr. 23, 1996

[54] ORAL SUCTION TIP

[75] Inventors: Ronald L. S. Whitehouse; Connie Watson, both of Edmonton, Alberta, Canada

[73] Assignee: White Shield Inc., Edmonton, Canada

[21] Appl. No.: 382,975

[22] Filed: Feb. 3, 1995

[51] Int. Cl.$^6$ .................................................. A61C 17/06
[52] U.S. Cl. ............................................. 433/95; 433/96
[58] Field of Search .................. 433/91, 93, 94, 433/95, 96; 604/119, 902

[56] References Cited

U.S. PATENT DOCUMENTS

| | | | |
|---|---|---|---|
| 1,222,267 | 4/1917 | Cosad | 433/91 |
| 1,388,312 | 8/1921 | Seeger | 433/96 |
| 1,930,196 | 10/1933 | Fisher | 433/94 |
| 3,453,735 | 7/1969 | Burt | 433/96 |
| 3,455,324 | 7/1969 | Bieri et al. . | |
| 3,516,160 | 7/1970 | Leffler | 433/95 |
| 3,595,234 | 7/1971 | Jackson | 604/119 |
| 3,623,483 | 11/1971 | Dyer, Jr. | 604/902 |
| 3,881,254 | 5/1975 | Epstein | 433/96 |
| 4,158,916 | 6/1979 | Adler | 433/91 |
| 4,221,220 | 9/1980 | Hansen | 433/95 |
| 4,287,889 | 9/1981 | Stupar | 604/119 |
| 4,417,874 | 11/1983 | Anderson et al. | 433/96 |
| 5,080,587 | 1/1992 | Miyao | 433/91 |
| 5,094,616 | 3/1992 | Levenson | 433/91 |
| 5,123,840 | 6/1992 | Nates | 433/91 |
| 5,195,952 | 3/1993 | Solnit et al. | 433/91 |

FOREIGN PATENT DOCUMENTS 2058576  4/1981  United Kingdom .................. 433/95

OTHER PUBLICATIONS

Article published in The Journal of The American Dental Association vol. 124 Apr. 1993 entitled Possibility of Cross-Contamination Between Dental patients By Means of the Saliva Ejector by C. M. Watson R. D. H.; R. L. S. Whitehouse, PH.D.

*Primary Examiner*—Cary E. O'Connor
*Attorney, Agent, or Firm*—Anthony R. Lambert

[57] ABSTRACT

An oral suction tip is described which includes a tubular body. The tubular body has a peripheral sidewall, a first end, a second end, and a single passage for transmitting fluids extending between the first end and the second end. A mouthpiece is provided at the second end of the tubular body. At least one vacuum release aperture extends through the sidewall of the tubular body in direct communication with the fluid passage. The at least one vacuum release aperture is spaced from the mouthpiece, such that when the mouthpiece is inserted into a patient's mouth the at least one vacuum release aperture is not confined within the patient's mouth. A porous guard overlies in spaced relation the at least one vacuum release aperture. This prevents accidental blockage of the at least one vacuum release aperture and also prevents regulation of the suction by means of the at least one vacuum release aperture.

1 Claim, 1 Drawing Sheet

ORAL SUCTION TIP

FIELD OF THE INVENTION

The present invention relates to a form of oral suction tip which prevents a back flow of oral contaminants from a suction line into a patient's mouth.

BACKGROUND OF THE INVENTION

Dental suction lines have attached to their remote ends a disposable oral suction tip (also known as a "saliva ejector tip" or an "evacuator tip"). It is inserted into the patient's mouth for the purpose of drawing away excess fluids through the suction line. In the April 1993 edition of the Journal of the American Dental Association, Watson and Whitehouse published a paper entitled "Possibility of Cross-contamination between Dental Patients by means of the Saliva Ejector". This paper documented that, when a patient closes his or her lips around the oral suction tip, a higher vacuum can be temporarily created in the mouth than in the suction line and a back flow of fluid containing oral contaminants from the suction line into the mouth can occur.

Prior to the study by Watson and Whitehouse it had been felt that disposal and replacement of the oral suction tip between patients was sufficient protection for the patient. The study clearly showed the presence of alpha-haemolytic organisms, characteristic of oral flora, in the suction line after use. This raises the possibility of a cross-contamination occurring between patients, and demonstrates the need to re-evaluate sanitation and hygienic practises in dental offices.

The original study by Watson and Whitehouse was conducted with oral suction tips connected to low volume suction lines. A subsequent study by Watson and Whitehouse with the oral suction tips connected to high volume suction lines has determined that the back flow of oral contaminants is even more pronounced in high volume suction lines.

U.S. patent application Ser. No. 08/220,550 by Whitehouse and Watson relates to a method for preventing a back flow of oral contaminants in a suction line. The method involves placing an unregulated vacuum release aperture through a tubular sidewall of an oral suction tip. However, the method is not effective if the vacuum release aperture becomes blocked during use, and the patent contains a teaching that preventative measures should be taken to prevent such blockage from occurring.

SUMMARY OF THE INVENTION

What is required is an oral suction tip for which accidental blockage of the vacuum release aperture is unlikely, if not impossible. It is preferred that a deliberate attempt at regulation of suction by means of the vacuum release aperture be precluded.

According to the present invention there is provided an oral suction tip which is comprised of a tubular body. The tubular body has a peripheral sidewall, a first end, a second end, and a single passage for transmitting fluids extending between the first end and the second end. A mouthpiece is provided at the second end of the tubular body. At least one vacuum release aperture extends through the sidewall of the tubular body in direct communication with the fluid passage. The at least one vacuum release aperture is spaced from the mouthpiece, such that when the mouthpiece is inserted into a patient's mouth the at least one vacuum release aperture is not confined within the patient's mouth. A porous guard overlies in spaced relation the at least one vacuum release aperture. This prevents accidental blockage of the at least one vacuum release aperture and also prevents regulation of the suction by means of the at least one vacuum release aperture.

The presence of a porous guard makes it unlikely that the vacuum release aperture will ever become accidentally blocked. In order to make the guard porous there must be a plurality of passages to permit the free flow of air. It will be appreciated that porous guards can be constructed with such a great number of air passages that accidental blockage or even deliberate attempts at regulation can be made practically impossible. When determining the number of vacuum release apertures required and the size of such vacuum release apertures care must be exercised to ensure a sufficient release of vacuum to prevent a backflow of oral contaminants from the suction line while ensuring that the oral suction tip maintains sufficient suction to perform its intended function. Regardless of the number and configuration of vacuum release apertures, it is preferable that each vacuum release aperture be guarded in order to prevent accidental blockage or a deliberate attempt at regulating the suction by means of the vacuum release apertures.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
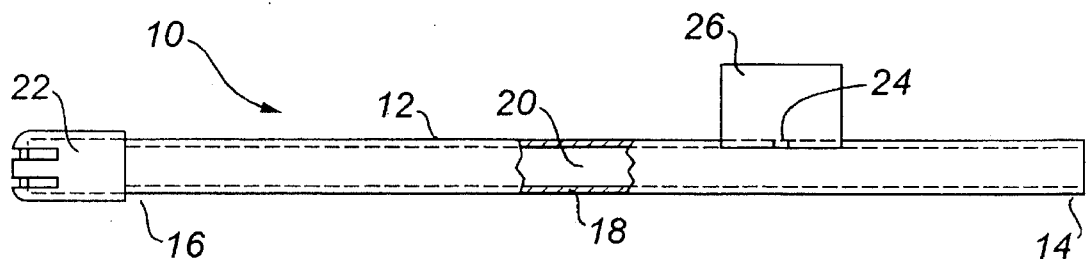
FIG. 1 is a side elevation view of an oral suction tip constructed in accordance with the teachings of the present invention.

The preferred embodiment, an oral suction tip generally identified by reference numeral 10, will now be described with reference to FIGS. 1 through 4.

Figure 2:
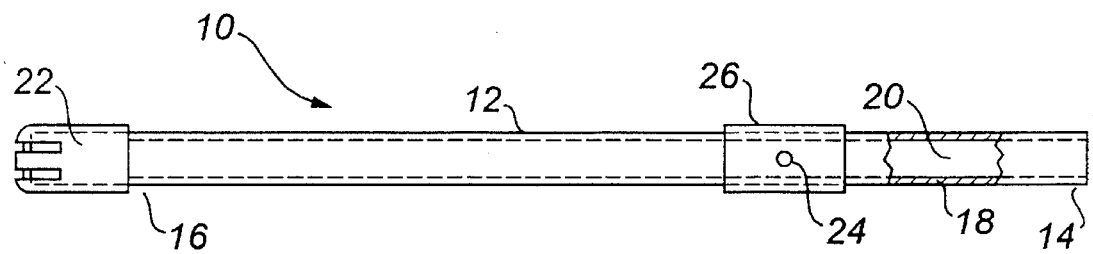
FIG. 2 is top plan view of the oral suction tip 5 illustrated in FIG. 1.
Figure 3:
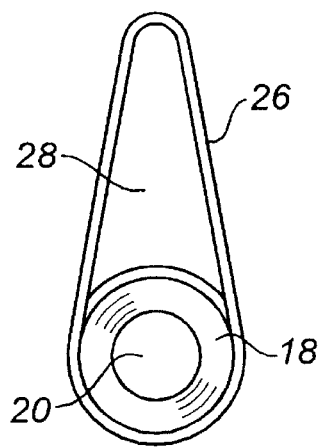
FIG. 3 is an end elevation view of a first end of the oral suction tip illustrated in FIG. 1.
Figure 4:
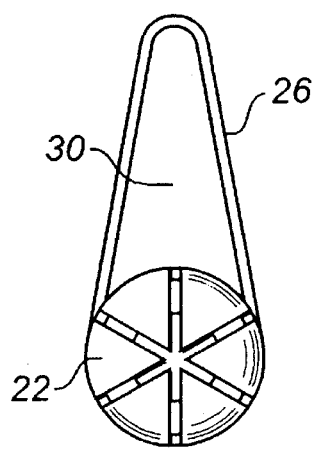
FIG. 4 is an end elevation view of a second end of the oral suction tip illustrated in FIG. 1.

Referring to FIGS. 1 through 4, oral suction tip 10 consists of a tubular body 12. Referring to FIGS. 1 and 2, tubular body 12 has a first end 14 and a second end 16. Referring to FIG. 3, tubular body 12 has a peripheral sidewall 18 and a single passage 20 for transmitting fluids. Referring to FIGS. 1 and 2, fluid passage 20 (shown in dotted lines) extends between first end 14 and second end 16. Referring to FIGS. 1, 2, and 4, a mouthpiece 22 is provided at second end 16 of tubular body 12. Referring to FIGS. 1 and 2, one vacuum release aperture 24 is provided which is spaced from mouthpiece 22. Referring to FIG. 1, vacuum release aperture 24 extends through sidewall 18 of tubular body 12 in direct communication with fluid passage 20. Referring to FIGS. 1 through 4, a porous guard 26 overlies in spaced relation vacuum release aperture 24. Two large air passages 28 and 30 extend through guard 26. Air passage 28 is illustrated in FIG. 3. Air passage 30 is illustrated in FIG. 4.

The use and operation of oral suction tip 10 will now be described with reference to FIGS. 1 through 4. In use, first end 14 of oral suction tip 10 is connected to a suction line (not shown). Mouthpiece 22, positioned at second end 16, is inserted into the patient's mouth. The presence of vacuum release aperture 24 prevents a back flow of oral contaminants. During dental procedures, it is not uncommon for dental personnel to push the oral suction tip to one side of a patient's mouth in order to provide more room for dental instruments. The patient is sometimes asked to assist by holding the oral suction tip to one side of his or her mouth. With prior art devices, there was always a danger that the patient or dental personnel would accidentally block the vacuum release aperture with their hands when handling the oral suction tip. Oral suction tip 10 corrects this problem. Vacuum release aperture 24 is guarded by porous guard 26. Guard 26, as illustrated, has two air passages 28 and 30, as illustrated in FIGS. 3 and 4. In the event of a blockage of air passage 28 air can still pass through air passage 30 to vacuum release aperture 24. This means that an accidental blockage of vacuum release aperture 24 cannot occur. By increasing the number of air passages, even a deliberate blockage of vacuum release passage 24 can be avoided.

It will be apparent to one skilled in the art that the key to the present invention is that guard 26 be porous in the sense that it must allow air to pass freely to vacuum release aperture 24. The illustrated embodiment with two large air passages 28 and 30 is preferred solely because it is inexpensive to manufacture. It will be appreciated, however, that guard 26 can be made more elaborate with a plurality of smaller air passages. It will finally be apparent to one skilled in the art that other modifications may be made to the illustrated embodiment without departing from the spirit and scope of the invention as hereinafter defined in the Claims.

The embodiments of the invention which an exclusive property or privilege is claimed are defined as follows:

1. An oral suction tip, comprising:
    a tubular body having a peripheral sidewall, a first end, a second end, and a single passage for transmitting fluids extending between the first end and the second end;
    a mouthpiece at the second end of the tubular body;
    at least one vacuum release aperture extending through the sidewall of the tubular body in direct communication with the fluid passage, the at least one vacuum release aperture being spaced from the mouthpiece such that when the mouthpiece is inserted into a patient's mouth the at least one vacuum release aperture is not confined within the patient's mouth; and
    a porous guard overlying in spaced relation the at least one vacuum release aperture, thereby preventing accidental blockage of the at least one vacuum release aperture and preventing regulation of the suction by means of the at least one vacuum release aperture.

* * * * *